(12) United States Patent
Gleitman

(10) Patent No.: US 8,961,006 B2
(45) Date of Patent: Feb. 24, 2015

(54) FIBER OPTIC SENSING SYSTEMS AND METHODS

(75) Inventor: Daniel D. Gleitman, Houston, TX (US)

(73) Assignee: WellDynamics, B.V., Leiderdorp (NL)

( * ) Notice: Subject to any disclaimer, the term of this patent is extended or adjusted under 35 U.S.C. 154(b) by 73 days.

(21) Appl. No.: 12/034,058

(22) Filed: Feb. 20, 2008

(65) Prior Publication Data
US 2008/0137711 A1 Jun. 12, 2008

Related U.S. Application Data

(60) Continuation of application No. 11/453,664, filed on Jun. 15, 2006, now abandoned, which is a division of application No. 10/461,977, filed on Jun. 13, 2003, now abandoned.

(51) Int. Cl.
*G01K 1/02* (2006.01)
*G01J 5/08* (2006.01)
*G01K 11/00* (2006.01)
*E21B 47/06* (2012.01)
(Continued)

(52) U.S. Cl.
CPC ............... *E21B 47/065* (2013.01); *E21B 47/06* (2013.01); *E21B 47/123* (2013.01); *G01K 13/02* (2013.01); *G01N 21/645* (2013.01); *G01N 21/71* (2013.01); *G01N 21/77* (2013.01); *G01N 2021/7786* (2013.01)
USPC ........... 374/136; 374/120; 374/132; 374/141; 374/161

(58) Field of Classification Search
CPC ..................... G01N 21/274; G01N 2021/7786; G01N 21/71; G01N 2021/855; G01K 13/02
USPC ................... 374/136, 137, 141, 142, 120, 29, 374/43–44, 57, 135, 16, 24, 54, 17, 374/130–132, 161; 356/43; 250/269.1; 702/11, 12
See application file for complete search history.

(56) References Cited

U.S. PATENT DOCUMENTS

| 2,217,708 A | 10/1940 | Domer |
| 4,046,100 A | 9/1977 | Kuonen et al. |

(Continued)

FOREIGN PATENT DOCUMENTS

| GB | 02382136 | 5/2003 |
| JP | 58162824 | 9/1983 |

(Continued)

OTHER PUBLICATIONS

Emery L. Moore, "Temperature Distribution Measurement Using Raman Ration Thermometry." Fiber Optic and Laser Sensors III, Proceedings of SPIE, vol. 566, dated Aug. 1985.

(Continued)

*Primary Examiner* — Gail Kaplan Verbitsky
(74) *Attorney, Agent, or Firm* — Smith IP Services, P.C.

(57) ABSTRACT

Fiber optic sensing systems and methods. In a described embodiment, a fiber optic sensing system includes an optical fiber transmitting energy to a chemical vapor deposited diamond material proximate a substance in a well. The diamond material is deposited as a coating on a substrate. The substrate and coating are heated when the energy is transmitted by the optical fiber. This heats the substance in the well, which is detected to determine a property of the substance. In another embodiment, light energy is transmitted through the diamond material.

45 Claims, 4 Drawing Sheets

(51) Int. Cl.

| | |
|---|---|
| *E21B 47/12* | (2012.01) |
| *G01K 13/02* | (2006.01) |
| *G01N 21/64* | (2006.01) |
| *G01N 21/71* | (2006.01) |
| *G01N 21/77* | (2006.01) |

(56) References Cited

U.S. PATENT DOCUMENTS

| | | | |
|---|---|---|---|
| 4,302,970 A | 12/1981 | Snitzer et al. | |
| 4,375,164 A | 3/1983 | Dodge et al. | |
| 4,437,761 A * | 3/1984 | Kroger et al. | 356/44 |
| 4,537,067 A | 8/1985 | Sharp et al. | |
| 4,560,286 A * | 12/1985 | Wickersheim | 374/131 |
| 4,575,260 A * | 3/1986 | Young | 374/136 |
| 4,621,929 A | 11/1986 | Phillips | 374/43 |
| 4,676,664 A * | 6/1987 | Anderson et al. | 374/136 |
| 4,703,175 A | 10/1987 | Salour et al. | |
| 4,710,033 A | 12/1987 | Hirano et al. | |
| 4,729,668 A | 3/1988 | Angel et al. | |
| 4,756,627 A | 7/1988 | Nelson | |
| 4,776,827 A | 10/1988 | Greaves | |
| 4,778,987 A | 10/1988 | Saaski et al. | |
| 4,789,992 A | 12/1988 | Wickersheim et al. | |
| 4,819,658 A | 4/1989 | Kolodner | |
| 4,895,156 A | 1/1990 | Schulze | |
| 4,906,107 A | 3/1990 | Luukkala | |
| 4,925,701 A * | 5/1990 | Jansen et al. | 427/575 |
| 4,976,142 A | 12/1990 | Perales | |
| 4,986,671 A * | 1/1991 | Sun et al. | 374/131 |
| 4,988,212 A | 1/1991 | Sun et al. | |
| 5,004,013 A | 4/1991 | Beaston | |
| 5,052,820 A | 10/1991 | McGinniss et al. | |
| 5,112,137 A | 5/1992 | Wickersheim et al. | |
| 5,115,127 A * | 5/1992 | Bobb et al. | 250/227.19 |
| 5,159,569 A | 10/1992 | Xu et al. | |
| 5,163,321 A | 11/1992 | Perales | |
| 5,165,292 A | 11/1992 | Prohaska | |
| 5,201,022 A * | 4/1993 | Shifflett | 385/128 |
| 5,212,099 A | 5/1993 | Marcus | |
| 5,271,469 A | 12/1993 | Brooks et al. | |
| 5,348,093 A | 9/1994 | Wood et al. | |
| 5,355,425 A * | 10/1994 | Braiman et al. | 385/31 |
| 5,364,186 A | 11/1994 | Wang et al. | |
| 5,378,343 A | 1/1995 | Kounaves et al. | |
| 5,385,404 A * | 1/1995 | Jones | 374/161 |
| 5,399,868 A | 3/1995 | Jones et al. | |
| 5,641,230 A | 6/1997 | Okubo | |
| 5,663,556 A | 9/1997 | Wessels et al. | |
| 5,721,492 A | 2/1998 | Saenger | |
| 5,758,968 A | 6/1998 | Diebold | |
| 5,803,607 A | 9/1998 | Jones et al. | |
| 5,821,861 A * | 10/1998 | Hartog et al. | 340/584 |
| 5,839,830 A * | 11/1998 | Young et al. | 374/161 |
| 5,876,119 A | 3/1999 | Ishikawa et al. | |
| 5,933,565 A | 8/1999 | Diebold | |
| 6,005,242 A | 12/1999 | Chernyak | |
| 6,164,817 A | 12/2000 | Trainer | |
| 6,223,588 B1 | 5/2001 | Burgass et al. | |
| 6,281,489 B1 | 8/2001 | Tubel et al. | |
| 6,283,632 B1 | 9/2001 | Takaki | |
| 6,324,904 B1 | 12/2001 | Ishikawa et al. | |
| 6,354,147 B1 | 3/2002 | Gysling et al. | |
| 6,408,943 B1 | 6/2002 | Schultz et al. | |
| 6,422,084 B1 | 7/2002 | Fernald et al. | |
| 6,452,667 B1 | 9/2002 | Fernald et al. | |
| 6,467,340 B1 | 10/2002 | Gallagher et al. | |
| 6,480,000 B1 | 11/2002 | Kong et al. | |
| 6,490,931 B1 | 12/2002 | Fernald et al. | |
| 6,497,279 B1 | 12/2002 | Williams et al. | |
| 6,511,222 B1 | 1/2003 | Bouamra | |
| 6,540,021 B1 | 4/2003 | Botrel | |
| 6,568,846 B1 | 5/2003 | Cote et al. | |
| 6,644,848 B1 | 11/2003 | Clayton et al. | |
| 6,719,049 B2 | 4/2004 | Sherwood et al. | |
| 6,726,360 B2 | 4/2004 | Singh et al. | |
| 6,769,805 B2 | 8/2004 | Williams et al. | |
| 6,772,085 B2 | 8/2004 | Watkins et al. | |
| 6,796,710 B2 | 9/2004 | Yates et al. | |
| 6,807,854 B2 | 10/2004 | Peysson et al. | |
| 6,847,034 B2 * | 1/2005 | Shah et al. | 250/269.1 |
| 6,986,294 B2 * | 1/2006 | Fromme et al. | 73/865.8 |
| 2002/0006153 A1 | 1/2002 | Ranson et al. | |
| 2002/0007945 A1 | 1/2002 | Neuroth et al. | |
| 2002/0063866 A1 | 5/2002 | Kersey et al. | |
| 2002/0064206 A1 | 5/2002 | Gysling et al. | |
| 2002/0154028 A1 | 10/2002 | Beique et al. | |
| 2002/0174728 A1 | 11/2002 | Beresford et al. | |
| 2003/0056581 A1 | 3/2003 | Turner et al. | |
| 2003/0112848 A1 | 6/2003 | Khan | |
| 2003/0126921 A1 | 7/2003 | Zisk et al. | |
| 2003/0205083 A1 | 11/2003 | Tubel et al. | |
| 2003/0219190 A1 | 11/2003 | Pruett | |
| 2003/0234921 A1 | 12/2003 | Yamate et al. | |
| 2004/0112848 A1 | 6/2004 | Ito | |
| 2004/0154390 A1 * | 8/2004 | Baustad | 73/152.55 |
| 2004/0240515 A1 | 12/2004 | Egan et al. | |
| 2004/0244970 A1 | 12/2004 | Smith | |
| 2004/0252748 A1 | 12/2004 | Gleitman | |
| 2005/0152432 A1 | 7/2005 | Hakimuddin | |
| 2006/0146909 A1 | 7/2006 | Morse et al. | |
| 2006/0214098 A1 * | 9/2006 | Ramos | 250/256 |
| 2006/0233217 A1 | 10/2006 | Gleitman | |
| 2006/0245469 A1 | 11/2006 | Koeniger | |

FOREIGN PATENT DOCUMENTS

| | | |
|---|---|---|
| JP | 58102357 | 12/1984 |
| WO | 9945235 | 9/1999 |
| WO | 0104581 | 1/2001 |

OTHER PUBLICATIONS

Ernest O. Doebelin, "Measurement Systems Application and Design," McGraw-Hill, dated 1976, pp. 448-462.
Koheras product catalog, 7 pgs., dated Jan. 2003.
J.L. Davidson, Vanderbilt University Publication, date unknown, 3 pgs.
Vanderbilt University, "Diamond: Crown Jewel of Microelectronics," Engineering News Newsletter, dated 2002.
Vanderbilt University, "Diamond Research and Development," About Research Newsletter, dated 2002.
Cidra Corporation, "Sonartrac Clamp-on Flow Meter," dated 2003.
Sensa, "Flow Rate Measurement," dated 2003.
Timothy J. Cowles, et al., "In Situ Monitoring of Ocean Chlorophyll via Laser-Induced Flourescence Backscattering Through an Optical fiber," Applied Optics, vol. 28, No. 3, dated Feb. 1989.
R.G. Miltimothy J. Cowles, et al., "In Situ Measurement Using an Optical Fibre Array Fluorosensor," SPIE vol. 2838, date unknown.
Office Action for U.S. Appl. No. 10/461,977, dated Apr. 21, 2006.
Office Action for U.S. Appl. No. 10/461,977, dated Aug. 10, 2005.
Office Action for U.S. Appl. No. 10/461,977, dated Feb. 24, 2005.
Office Action for U.S. Appl. No. 10/461,977, dated Aug. 25, 2004.
Office Action for U.S. Appl. No. 10/461,977, dated Jun. 29, 2004.
Office Action for U.S. Appl. No. 11/453,664, dated Oct. 6, 2006.
Office Action for U.S. Appl. No. 11/453,664, dated Feb. 8, 2007.
Office Action for U.S. Appl. No. 11/453,664, dated Sep. 25, 2007.

* cited by examiner

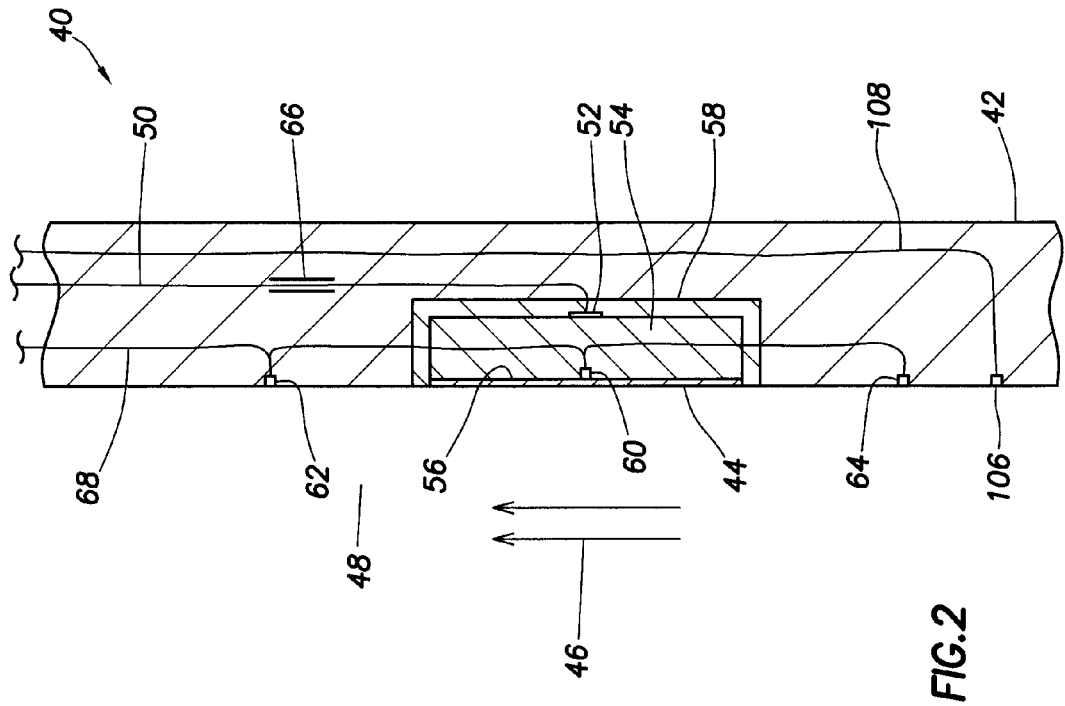
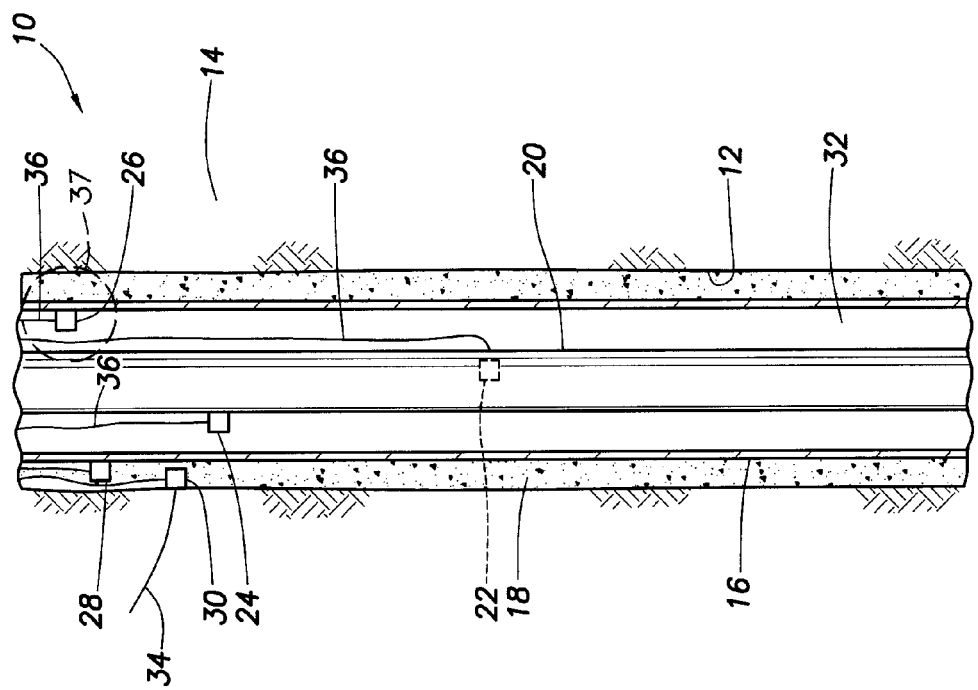

FIBER OPTIC SENSING SYSTEMS AND METHODS

CROSS-REFERENCE TO RELATED APPLICATIONS

The present application is a continuation of U.S. application Ser. No. 11/453,664, filed Jun. 15, 2006, now abandoned which is a divisional of U.S. application Ser. No. 10/461,977, filed Jun. 13, 2003 now abandoned. The entire disclosures of these prior applications are incorporated herein by this reference.

BACKGROUND

The present invention relates generally to equipment utilized and operations performed in conjunction with a subterranean well and, in an embodiment described herein, more particularly provides a fiber optic sensing system and method for measuring properties, such as heat transfer characteristics, of substances and environments in wells and other locations.

It is frequently desirable to be able to detect or measure various properties of substances in a well. For example, it may be desirable to determine a rate of flow of fluid from a producing zone, determine the composition of a fluid mixture in the well, evaluate the quality of a cementing operation, locate a fluid interface (i.e., liquid/liquid or gas/liquid) in the well or in a formation intersected by the well, etc.

Typically, certain measurements are made by conveying a logging tool into the well and using sensors, such as flowmeters and thermocouples, to detect properties of fluid in the well. Unfortunately, the logging tool obstructs a passage for flow of fluid in the well, thereby interfering with production. It is also somewhat time-consuming and costly to make such logging trips into the well. This is particularly so if it is desired to periodically perform the measurements to track changes in the well over time, such as to evaluate the migration of an oil/water interface in a formation drained by the well.

Some fiber optic measurement systems have been developed for permanent installation in a well. However, these are very expensive, and their principles of operation make the measurements obtained using these systems possibly unreliable at certain flow rates, flow regimes and/or hydrocarbon combinations, etc.

Therefore, it may be seen that it would be beneficial to provide improved systems and methods for sensing properties of substances in a well. These systems and methods would preferably, but not necessarily, eliminate any obstruction to fluid flow through the well, be configured for permanent installation in the well, be convenient in use and provide reliable results.

Furthermore, it would be desirable for such systems and methods to be versatile in application to, for example, pipelines, chemical processes, on the surface, remotely controlled and/or monitored, etc. Other examples include production infrastructure immediately downstream of a well, e.g., sea bed flowlines and manifolds, subsea or surface wellheads, risers and production platform pipes. Sensing systems installed at these locations may be used along with other sensors for monitoring of production parameters, as well as formation and deposition of waxes, asphaltines and hydrates.

SUMMARY

In carrying out the principles of the present invention, in accordance with an embodiment thereof, fiber optic sensing systems and methods are provided which solve one or more of the above problems in the art. A sensing system described herein is suitable for permanent installation in a well, does not interfere with fluid flow or production, and utilizes a unique method of operation to detect properties of substances in the well.

In one aspect of the invention, a fiber optic sensing system for sensing at least one property of a substance is provided. The system includes a sensor surface in contact with the substance. An optical fiber transmits energy to the sensor surface. The sensor surface, in turn, transmits energy to the substance.

In another aspect of the invention, a fiber optic sensing system for use in detecting at least one property of a substance in a well is provided. The sensing system includes a sensor surface configured for contacting the substance in the well, an optical fiber for transmitting energy to the sensor surface and a temperature sensor for detecting a temperature of the substance. The sensor surface is heated when energy is transmitted by the optical fiber.

In yet another aspect of the invention, another fiber optic sensing system is provided. The sensing system includes a sensor surface configured for contacting the substance in the well and an optical fiber for transmitting light energy to the sensor surface. The light energy is transmitted from the optical fiber through the sensor surface and to the substance. The light energy produces a response in the substance, such as a temperature change, fluorescence or a spectral emission.

In still another aspect of the invention, a method of detecting at least one property of a substance in a well is provided. The method includes the steps of: positioning a sensor surface in the well in contact with the substance; transmitting energy through an optical fiber to the sensor surface, thereby heating the sensor surface and the substance in contact with the sensor surface; and detecting a temperature of the heated substance.

In a further aspect of the invention, another method of detecting at least one property of a substance in a well is provided. The method includes the steps of: positioning a sensor surface in the well in contact with the substance; transmitting light energy through an optical fiber to the sensor surface; transmitting the light energy through the sensor surface to the substance; and detecting a response of the substance to the transmitted light energy.

These and other features, advantages, benefits and objects of the present invention will become apparent to one of ordinary skill in the art upon careful consideration of the detailed description of representative embodiments of the invention hereinbelow and the accompanying drawings.

BRIEF DESCRIPTION OF THE DRAWINGS

FIG. 1 is a schematic partially cross-sectional view of a first fiber optic sensing system embodying principles of the present invention;

FIG. 2 is an enlarged schematic cross-sectional view of a first fiber optic sensor embodying principles of the present invention;

DETAILED DESCRIPTION

Figure 4:
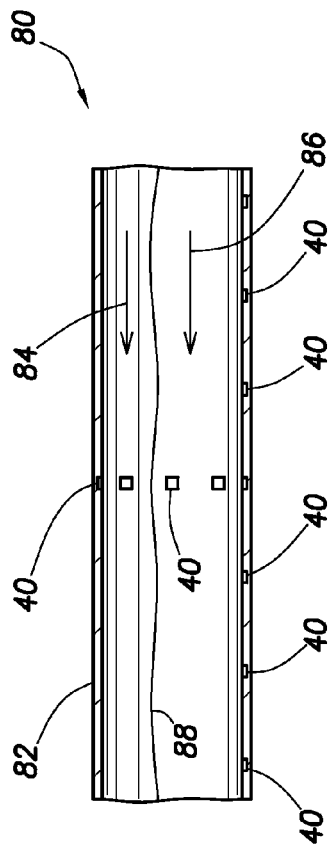
FIG. 4 is a schematic cross-sectional view of a second fiber optic sensing system embodying principles of the present invention.

Representatively and schematically illustrated in FIG. 1 is a fiber optic sensing system 10 which embodies principles of the present invention. In the following description of the system 10 and other apparatus and methods described herein, directional terms, such as "above", "below", "upper", "lower", etc., are used only for convenience in referring to the accompanying drawings. Additionally, it is to be understood that the various embodiments of the present invention described herein may be utilized in various orientations, such as inclined, inverted, horizontal, vertical, etc., and in various configurations, without departing from the principles of the present invention.

The sensing system 10 is depicted in FIG. 1 as being installed in a well which includes a wellbore 12 intersecting an earth formation 14. The wellbore 12 is lined with protective casing or liner 16. A hardenable material 18, such as cement, epoxy, etc., is positioned between the casing 16 and the wellbore 12.

As used herein, the terms "casing" and "liner" are used to indicate any protective wellbore lining including, but not limited to, segmented or continuous tubular strings, rigid or expandable structures, made from steel, plastics or any other material, etc.

A tubular string 20, such as a production tubing string, is positioned in the casing 16 for flowing fluids from the well to the earth's surface, subsea wellhead, etc. However, it should be clearly understood that the principles of the invention may be practiced in circumstances other than a producing well, such as in an injection well or a combined production and injection well.

A fiber optic sensing device 22 is positioned in the tubular string 20 to detect properties of fluid flowing through the tubular string. Another fiber optic sensing device 24 is positioned external to the tubular string 20 to detect properties of the tubular string itself and/or to detect properties of fluid in an annulus 32 external to the tubular string. In actual practice, the sensing devices 22, 24 would preferably be configured so that they are disposed in a sidewall of the tubular string 20.

Another fiber optic sensing device 26 is positioned within the casing 16 to detect properties of the casing itself and/or to detect properties of fluid disposed in the annulus 32 between the tubular string 20 and the casing. Another fiber optic sensing device 28 is positioned external to the casing 16 to detect properties of the cement 18 and/or properties of fluids in the cement. In actual practice, the sensing devices 26, 28 would preferably be configured so that they are disposed in a sidewall of the casing 16.

Yet another fiber optic sensing device 30 is positioned adjacent the formation 14 to detect properties of the formation itself and/or to detect properties of fluid in the formation. For example, the sensing device 30 may be used to detect the progress or presence of a fluid interface 34 in the formation 14, such as an oil/water interface. In actual practice, the sensing device 30 may be conveyed into the well attached to the casing 16, or the sensing device could be flowed into the well along with the cement 18 as described in U.S. Pat. No. 6,408,943, the entire disclosure of which is incorporated herein by this reference.

The sensing system 10 illustrated in FIG. 1 includes the various sensing devices 22, 24, 26, 28, 30 to demonstrate the broad variety of applications of the principles of the invention to the problems of detecting properties of substances in a well. An actual well installation would not necessarily include all of the sensing devices 22, 24, 26, 28, 30, and might include other sensing devices which embody principles of the invention. It is also not necessary for the well to be cased, to have any tubular string therein, or to be a production well. Thus, it should be clearly understood that the sensor system 10 depicted in FIG. 1 is given only as an example of some of the uses of the inventive concepts described below, and these inventive concepts are in no way limited to the specific details of the sensor system of FIG. 1.

It will be appreciated that the sensing devices 22, 24, 26, 28, 30 detect properties of a variety of substances in the well. These substances are: 1) fluid flowing through the tubular string 20, 2) the tubular string itself, 3) fluid in the annulus 32 external to the tubular string, 4) the casing 16, 5) the cement 18, 6) fluid in the cement, 7) the formation 14, and 8) fluid in the formation. Of course, properties of substances other than, or in addition to, these may be detected without departing from the principles of the invention. In addition, or alternatively, the sensing devices 22, 24, 26, 28, 30 may detect properties of the environment or location, such as heat capacity, heat transfer, etc.

The sensing devices 22, 24, 26, 28, 30 are described herein as "fiber optic" sensing devices, since they each include an optical fiber 36 connected thereto for operation of the sensing device. An individual optical fiber 36 is illustrated for each of the sensing devices 22, 24, 26, 28, 30 in FIG. 1, but a single optical fiber may be used for more than one sensing device, if desired. For example, known optical multiplexing techniques may be used to permit multiple downhole sensing devices to be operated and/or communicated with via a single optical fiber.

The optical fiber 36 may be installed in a capillary tube inside or outside of the tubular string 20, before or after the capillary tube is installed in the well, for example, as described in U.S. Pat. Nos. 5,163,321 and 4,976,142, the disclosures of which are incorporated herein by this reference. The sensing devices 22, 24, 26, 28, 30 may be connected to the optical fiber 36 before or after installation in the well, for example, the optical fiber may be "stabbed into" the sensing devices after they are installed in the well. Furthermore, the optical fiber 36 and/or any of the sensors 22, 24, 26, 28, 30 may be integrated into the construction of any structure in the well, for example, integrated into the sidewall of a tubular string as described in U.S. Patent Application Publication No. 2002/0007945, the entire disclosure of which is incorporated herein by this reference.

Figure 8:
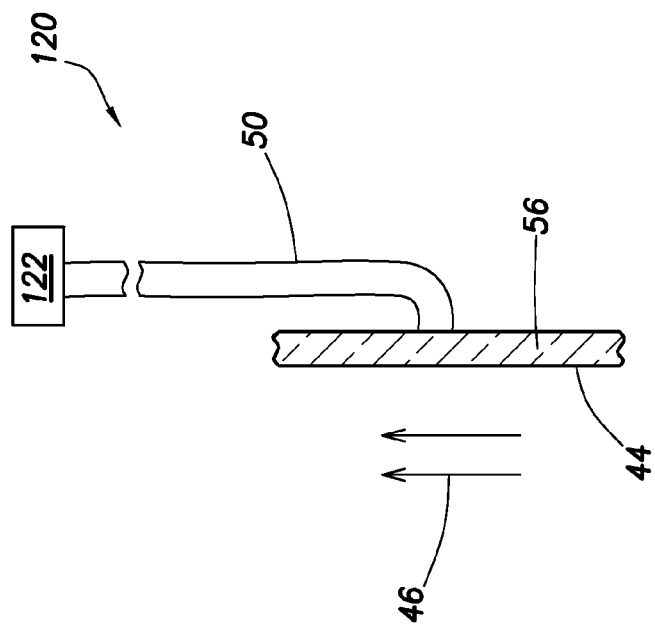
FIG. 8 is a schematic cross-sectional view of a third fiber optic sensor embodying principles of the present invention.

The sensing system 10 utilizing the optical fiber 36 and one or more of the sensing devices 22, 24, 26, 28, 30 will typically also include an instrument at the surface or another remote location (not shown in FIG. 1, but see the detector 122 depicted in FIG. 8). The instrument may provide light energy, receive the sensing device(s) response, perform signal analysis, including optical signal processing, and may be packaged in one or more individual components in one or more physical locations, etc. For example, a single instrument may be used in conjunction with a single optical fiber 36, multiple instruments may be used in conjunction with multiple optical fibers, and any combination thereof.

Referring additionally now to FIG. 2, a fiber optic sensing device 40 embodying principles of the invention is representatively illustrated. The sensing device 40 may be used for any of the sensing devices 22, 24, 26, 28, 30 described above, or the sensing device 40 may be used in other sensing systems. The sensing device 40 is depicted as being positioned in a sidewall of a tubular string 42, such as the tubular string 20 or casing 16 depicted in FIG. 1, but it should be understood that the sensing device may be otherwise positioned in keeping with the principles of the invention.

As shown in FIG. 2, a surface 44 of the sensing device 40 is positioned in contact with a fluid (indicated by arrows 46) flowing through a passage 48 in the tubular string 42. This configuration corresponds to the sensing device 22 in the tubular string 20, or the sensing device 26 in the casing 16, in FIG. 1. Alternatively, the fluid 46 could be external to the tubular string 42, with the surface 44 of the sensing device 40 facing outwardly, which would correspond to the sensing device 24 on the tubular string 20, or to the sensing device 28 on the casing 16, as depicted in FIG. 1.

An optical fiber 50 extends from a remote location, such as the earth's surface or another location in the well, to an energy converter 52. Light energy transmitted through the optical fiber 50 is converted to heat in a substrate 54 by the converter 52. For example, the converter 52 may be a black body interface, or another type of converter.

However, it should be clearly understood that an interface between the optical fiber 50 and the substrate 54 is not necessarily a black body or any type of separate converter 52. Instead, the optical fiber 50 could be connected directly to the substrate 54 (as depicted for the sensing device 120 in FIG. 8). Other connection or interface methods may also be used in keeping with the principles of the invention, for example, the substrate 54 could have a coating integrally formed therewith, etc.

Heat produced at the converter 52 is used to increase the temperature of the substrate 54, which in turn heats a coating 56 on an exterior side of the substrate. The converter 52 could be a special black surface on the coating 56, or the converter could be a structure interposed between the optical fiber 50 and the substrate 54. The heated coating 56, in turn, heats the fluid 46, which enables at least one property of the fluid to be detected, as described in more detail below.

As used herein, the term "coating" is used to indicate an outer layer or region of material, and is not used to specify any particular technique of producing such a layer or region. Coatings may be produced by any process, such as heat treatment, chemical treatment, application of a different material to a substrate, etc.

In order for the heat produced at the converter 52 to be transmitted efficiently to the fluid 46, the substrate 54 and coating 56 are preferably made of highly thermally conductive materials and are insulated from the tubular string 42 by insulation 58. However, if the tubular string 42 is made of a low thermal conductivity material, such as a composite material, or in other circumstances, the insulation 58 may not be used.

The substrate 54 may be made of a metallic material, such as steel. The coating 56 is preferably made of a material which is very durable, relatively erosion resistant, relatively hard, as well as being highly thermally conductive, since it is exposed to the flow of the fluid 46. A material suitable for use in the coating 56 is a diamond material. The diamond material is preferably attached to the substrate 54 by chemical vapor deposition, since this results in a reproducible uniform thickness of the diamond material which is permanently bonded to the substrate 54.

It should be understood, however, that other materials may be used for the substrate 54 and coating 56, if desired. In fact, it is not necessary for the substrate 54 material and the coating 56 material to be different materials. Thus, it is not necessary for the sensing device 40 to include a separate substrate 54 (for example, as depicted for the sensing device 120 in FIG. 8).

As the fluid 46 flows past the surface 44, the fluid is heated as described above. A temperature sensor 60, such as a thermocouple or a fiber optic temperature sensor (for example, a Bragg grating-type sensor), detects the temperature of the coating 56. Due to the high thermal conductivity of the coating 56, the fluid 46 in direct contact with the surface 44 should reach approximately the same temperature as the coating, but if a more direct measurement of the fluid temperature proximate the surface is desired, the sensor 60 may be positioned so that it is in direct contact with the fluid.

Another temperature sensor 62 is positioned downstream from the surface 44, and yet another temperature sensor 64 is positioned upstream from the surface. The sensors 60, 62, 64 are depicted in FIG. 2 as being connected to a single fiber optic line 68 extending to a remote location, such as to the instrument at a remote location as discussed above. However, separate lines may be used for the individual sensors 60, 62, 64, and other types of lines (such as electrical lines), power supply and communications may be used, without departing from the principles of the invention.

It should be understood that it is not necessary for all of the temperature sensors 60, 62, 64 to be included in the fiber optic sensing device 40, but the use of these temperature sensors does permit a significant number of properties of the fluid 46 to be detected. For example, use of the temperature sensors 62, 64 upstream and downstream of the surface 44 permits the direction of flow of the fluid 46 to be determined. The fluid 46 will have an increased temperature on the downstream side of the surface 44. As depicted in FIG. 2, the temperature sensor 62 will detect an increased temperature of the fluid 46, whereas the sensor 64 will not. If the flow of the fluid 46 were reversed, the sensor 64 would detect the increased temperature of the fluid 46.

If a known, controlled, constant intensity of light energy is transmitted through the optical fiber 50, the coating 56 will eventually reach an elevated equilibrium temperature, detected by the sensor 60. This equilibrium temperature is related to the velocity of the flow (or flow rate) of the fluid 46 past the surface 44, as well as being related to other properties of the fluid. Thus, if the light energy intensity and the coating 56 temperature are known, the fluid 46 flow rate may be determined.

The other properties of the fluid 46 may be determined by utilization of the sensing device 40, as well. For example, the sensors 60, 64 may be used to determine the density and thermal characteristics of the fluid 46. By detecting (via the sensor 60) the heat energy transmitted to the fluid 46 proximate the surface 44, as compared to the ambient conditions sensed at the upstream sensor 64, the thermal conductivity of the fluid may be determined.

By detecting the difference between the temperature of the fluid 46 proximate the surface 44 and the temperature of the fluid at the upstream sensor 64, the density of the fluid may be determined. This temperature difference may also be used to determine the velocity of the fluid 46. If the density of the fluid 46 is determined, then the relative ratio of different liquids (e.g., oil/water) making up the fluid may be determined. Of course, the downstream sensor 62 may be used in place of the upstream sensor 64 in these determinations of thermal conductivity, velocity, composition, etc., when flow direction is reversed.

Those skilled in the art will recognize that such determinations of density, velocity, identity, composition, etc. depend on known fluid mechanics and heat transfer relationships. Calculations of these properties may require reasonable assumptions to be made and/or measurement of additional variables, etc., to make accurate determinations.

An alternate technique would be to vary the intensity of the light energy transmitted through the optical fiber 50. For example, a fiber laser 66 interconnected to the optical fiber 50 may be cycled on and off. The laser 66 may be positioned downhole as depicted in FIG. 2, or it may be positioned at a remote location, such as the earth's surface. Of course, another type of light energy source or laser may be used instead of, or in addition to, the laser 66.

When the laser 66 is on, the coating 56 will reach an elevated equilibrium temperature. When the laser 66 is off, the coating 56 temperature will reduce to another equilibrium temperature. By detecting multiple sets of these elevated and reduced equilibrium temperatures, more accurate determinations may be made as to the properties of the fluid 46.

As another alternative, the coating 56 may be heated to an elevated equilibrium temperature by turning the laser 66 on. Then, with the laser 66 turned off, the transient decline in temperature of the coating 56 over time is detected by the sensor 60. This cooling versus time data may then be used in determining the velocity, density, composition, etc. of the fluid 46.

A transient increase in temperature of the coating 56 over time could also be used. Transient cooling and/or heating measurements could be combined with steady state measurements for enhanced accuracy in the fluid property analysis.

Figure 3:
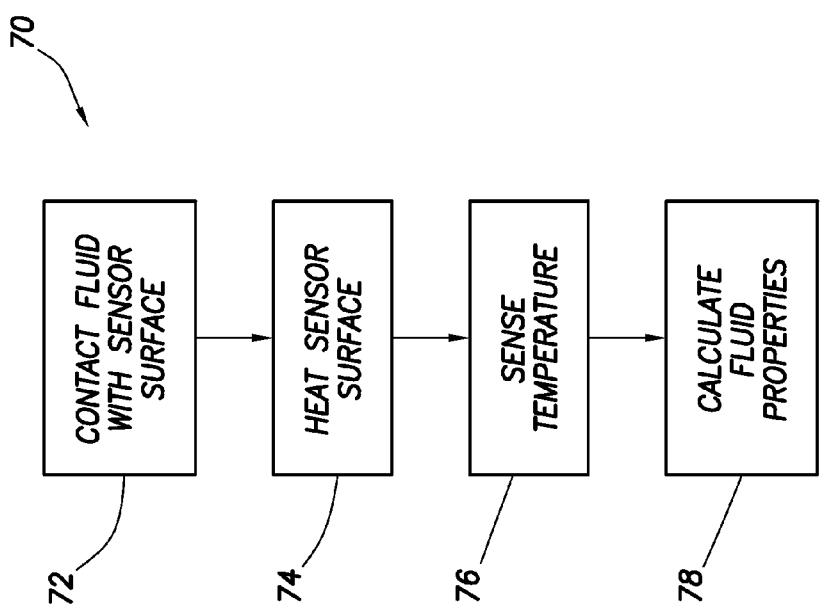
FIG. 3 is a flowchart of steps in a first method embodying principles of the present invention.

Referring additionally now to FIG. 3, a method 70 embodying principles of the invention is representatively illustrated with steps of the method in flowchart form. The method 70 has been described in part above in conjunction with the description of the sensing device 40. However, it should be understood that the method 70 may be used with other sensing devices without departing from the principles of the invention.

In step 72 of the method 70, a sensor surface is placed in contact with a fluid. The fluid may be the fluid 46 of FIG. 2, fluid in the annulus 32 of FIG. 1, fluid in the cement 18, fluid in the formation 14, etc. Alternatively, the sensor surface may be placed in contact with another substance, such as the tubular string 20 material, the casing 16 material, the cement 18, the formation 14, etc.

In step 74, the sensor surface is heated. As described above for the sensing device 40, light energy transmitted through the optical fiber 50 may be converted to heat energy to heat the sensor surface 44. By heating the sensor surface, the substance in contact with the sensor surface is also heated.

The light energy transmitted through the optical fiber 50 may be varied to produce variations in the response of the substance to the heating produced by the light energy. The response of the substance to this varied heating is indicative of properties of the substance, such as density, thermal conductivity, velocity, phase, composition (oil/water ratio, ratio of fluids produced from multiple zones), identity (zone of origin), the presence and/or progress of a fracture in a formation, a fluid interface in a formation (see FIG. 1) or in a well (see FIG. 4), integrity of a cementing operation (density of cement, presence of voids and cracks, migration of fluid through cement), etc.

The response may be qualitative or indicative of a trend over time. When combined with other data or modeling, the response may produce qualitative and quantitative results on which to base decisions concerning, for example, how production from the well or an injection program should be adjusted, etc.

The intensity of the light energy transmitted through the optical fiber 50 may be maintained constant, for example, to produce an equilibrium temperature of the coating 56 and/or of the substance in contact with the surface 44. For a given intensity of light energy transmitted through the optical fiber 50, the corresponding equilibrium temperature of the coating 56 and/or of the substance in contact with the surface 44 is indicative of properties of the substance, such as those discussed above. Multiple equilibrium temperatures for corresponding multiple light energy intensities may be obtained to increase the accuracy of the determination of properties of the substance.

Equilibrium temperatures in the coating 56 or substance may be produced by other methods, such as by varying the light energy in patterns or waves (square waves, sine waves, etc.). Multiple temperature equilibria may also be produced by maintaining the light energy constant and varying a fluid property, for example, by adjusting the flow rate using a choke, etc.

The light energy transmitted through the optical fiber 50 may be at times varied or cycled, and at times maintained constant. It is conceived that a combination of techniques will produce reliable "signatures" of the substance properties, so that they may be readily determined given the wealth of information provided by the sensing device 40. Obtaining these substance property "signatures" is an example of the type of empirical testing that a person skilled in the art would use to employ a new sensing device in a particular application. For example, production log measurements may be used to calibrate the "signatures," thereby eliminating, or at least reducing, the need to periodically run production logs.

For good heat transfer to the substance in contact with the sensor surface 44, a substrate 54 and chemical vapor deposited diamond material coating 56 have been described above. The diamond material in particular has a very high thermal conductivity and is very durable. However, it should be understood that the invention is not limited to use of any particular material or configuration of the structure used to transfer heat to the substance in contact with the surface 44.

In step 76 of the method 70, temperature is sensed. This may be the temperature of the substance in contact with the sensor surface, the temperature of the substance remote from the sensor surface, the temperature of the sensor surface, temperature change over time in the substance or sensor surface, or another temperature or combination of temperatures. Preferably, the sensed temperature(s) is indicative of a property of the substance in contact with the sensor surface, as discussed above.

Although certain types of temperature sensors have been described above, it should be understood that any type of sensor may be utilized to directly or indirectly detect a temperature in the sensing device 40. It is also conceived that the sensors may be positioned in any orientation or arrangement relative to the sensor surface 44 as may be determined to be appropriate for sensing a particular substance property. This is another example of the versatility of the sensing device 40, in that it may be configured as best suits the application.

In step 78, properties of the fluid or other substance are calculated using the sensed temperature(s) from step 76. A person of ordinary skill in the art, given the appropriate information (e.g., the configuration of the sensing device, well parameters, energy transmission, temperature data, etc.) will be able to determine the desired properties of the substance without undue experimentation. It should, however, be recognized that, for some of the substance properties to be calculated, some empirical parameters may need to be determined through controlled tests before accurate calculations may be made, the sensing device 40 configured and calibrated, etc.

Referring additionally now to FIG. 4, another fiber optic sensing system 80 is representatively and schematically illustrated. The sensing system 80 is similar in many respects to the sensing system 10 of FIG. 1, in that multiple sensing devices 40 are attached to a tubular member or string 82. In the sensing system 80, the sensing devices 40 are used to detect properties of fluids (indicated by arrows 84, 86) flowing through the tubular 82.

An interface 88 between the fluids 84, 86 may be detected by the sensing devices 40 which are circumferentially distributed about the tubular 82. The upper sensing devices 40 will detect one or more properties of the fluid 84 above the interface 88, and the lower sensing devices will detect one or more properties of the fluid 86 below the interface. This information may be useful where the tubular 82 is positioned in an at least substantially horizontal wellbore and the fluids 84, 86 are oil and water, or gas and oil, etc.

If the tubular 82 is not horizontal, a longitudinal location of the interface 88 may be determined using the sensing devices 40 which are distributed longitudinally on the tubular. These sensing devices 40 may also, or alternatively, be used to determine properties of the tubular 82 and/or the fluids 84, 86, such as thermal gradient along the tubular, thermal conductivity, density, heat transfer coefficient, heat capacity, etc.

Figure 5:
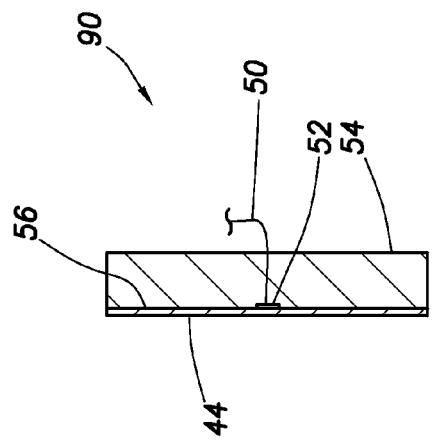
FIG. 5 is a schematic cross-sectional view of a second fiber optic sensor embodying principles of the present invention.

Referring additionally now to FIG. 5, another sensing device 90 is representatively and schematically illustrated. The sensing device 90 is very similar to the sensing device 40 described above, and so elements of the sensing device 90 which are similar to those previously described are indicated in FIG. 5 using the same reference numbers.

As depicted in FIG. 5, the sensing device 90 is separated from any structure on which it may be mounted, for clarity of illustration and description, and to emphasize that it is not necessary for any sensing device described herein to be attached to any particular structure, or any structure at all. For example, the sensing device 90 could be installed prior to cementing or flowed into the well with the cement 18 as shown for the sensor 30 in FIG. 1.

The sensing device 90 as depicted in FIG. 5 also does not have temperature sensors. It is not necessary for any sensing device described herein to have one or more temperature sensors in any particular configuration or arrangement relative to the surface 44. However, the sensing device 90 does preferably include at least one temperature sensor, which is not illustrated in FIG. 5.

The sensing device 90 does differ in at least one substantial respect from the sensing device 40, in that the optical fiber 50 extends to the converter 52, which is positioned adjacent the coating 56. This configuration may produce a more direct heating of the surface 44. The increased heating efficiency of the sensing device 90 may be desirable for use in some methods, such as the method 100 representatively illustrated in flowchart form in FIG. 6.

Figure 6:
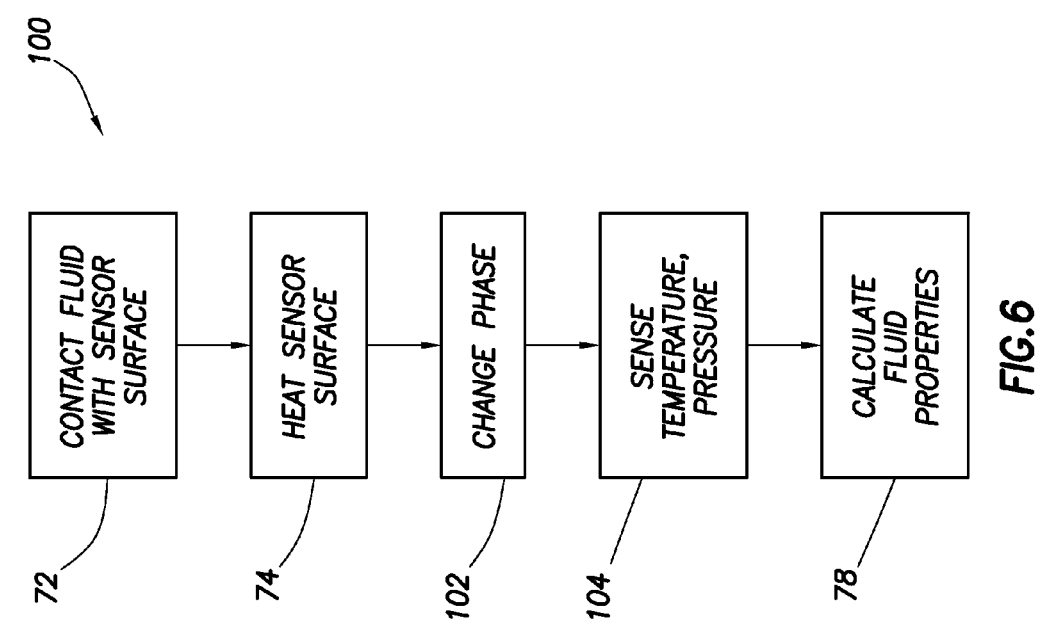
FIG. 6 is a flowchart of steps in a second method embodying principles of the present invention.

The method 100 is similar in many respects to the method 70 described above, and so steps of the method 100 which are similar to those previously described are indicated in FIG. 6 using the same reference numbers. In particular, steps 72, 74 and 78 are used in the method 100, for example, a substance in contact with the sensor surface 44 is subjected to a heat transfer detected by the sensing device 40, which is used to determine one or more properties of the substance.

However, in the method 100, a step 102 is used wherein a phase of the substance is changed. In many applications the substance of interest proximate to the sensor surface 44 is a fluid being produced from a formation. Under downhole conditions the fluid is often predominately a liquid phase (e.g., oil and/or water), and often includes a complex mixture of hydrocarbons, including dissolved gases and/or hydrocarbon fractions, which are liquid under downhole pressure, but at some combination of reduced pressure and/or increased temperature becomes gaseous. The heating of the sensor surface 44 and the fluid immediately proximate can, therefore, cause an evolution of gas from the liquid, i.e., a local phase change.

If the substance is initially a fluid, such as oil with gas dissolved therein, the heat transfer from the sensor surface 44 to the liquid causes a phase change, wherein the gas "bubbles" out of the liquid oil. This phase change (known as the "bubble point") is detected by the sensors in the sensing device 40 in step 104 of the method 100.

For example, one or more of the temperature sensors 60, 62, 64 may detect the change in heat transfer accompanying the phase change as the equilibrium temperature changes dramatically. Further, the sensing device 40 may include a pressure sensor 106 which detects the ambient hydrostatic or circulating pressure proximate the sensor surface 44. The pressure sensor 106 may be a fiber optic sensor (such as a fiber Bragg grating-type sensor), in which case an optical fiber 108 may extend to the sensor from a remote location.

This information may be used to determine the PVT (pressure/volume/temperature) characteristics of the fluid 46. Of course, the phase change may be reversed, performed multiple times, be between other phases (such as liquid/solid as in hardening cement, solid/liquid as in chemical treatment of paraffin accumulation), etc., in keeping with the principles of the invention. Wellbore fluids may be separately analyzed, for example, at a suitably equipped commercial laboratory, to precisely determine the PVT characteristics, and then this laboratory analysis may be used to calibrate the sensor measurements. Qualitative measurements may also be used, for example, to identify trends in the PVT characteristics over time.

Figure 7:
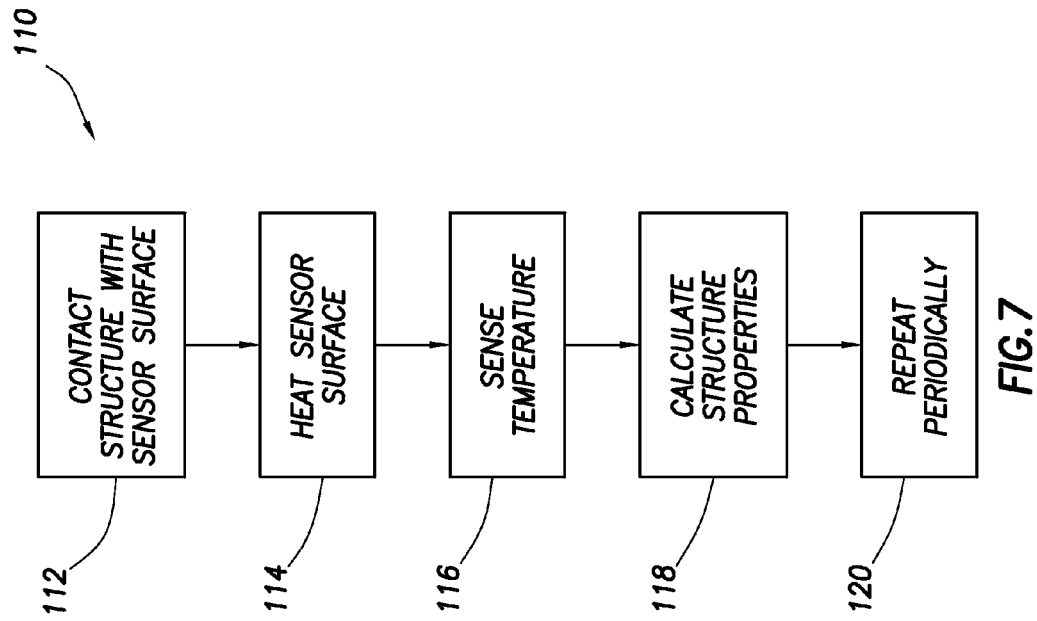
FIG. 7 is a flowchart of steps in a third method embodying principles of the present invention.

Referring additionally now to FIG. 7, another method 110 embodying principles of the invention is representatively illustrated. The method 110 is very similar to the method 70 of FIG. 3. One significant difference is that, in step 112 of the method 110, a structure (not necessarily a fluid) is in contact with the sensor surface 44, and it is desired to monitor properties of the structure over time. The sensor surface is heated in step 114, temperature is sensed in step 116, properties of the structure are calculated in step 118, and the method 110 is repeated periodically in step 120.

In the above description of the method 70, the step 72 was described as possibly being performed with the sensor surface 44 in contact with another substance, such as the tubular string 20 material, the casing 16 material, the cement 18, the formation 14, etc. The method 110 demonstrates how this may be accomplished for a particular application in which it is desired to monitor properties of a structure over time.

For example, it may be desired to monitor a physical property, such as stress or strain, or a thermal property of the tubular string 20 over an extended period. In FIG. 1, element 37 indicates a particular location which can be considered as a local thermal system of interest, wherein sensor 26 is used to detect the thermal properties of this thermal system which includes the formation 14, cement 18, casing 16, annulus 32, tubing 20, the proximate trapped and flowing fluids, and the associated thermal interfaces. The steps 112-118 could be performed each day, week or month, etc., to give an indication of how these properties change over time.

Another example would be placing the sensor surface 44 in contact with the formation 14 in order to detect properties of fluids in the formation. By monitoring the fluid properties in the formation 14 over time, the presence and progress of the fluid interface 34 through the formation, or other useful information, may be determined.

The steps 112-118 are very similar to the corresponding steps 72-78 of the method 70. The descriptions and variations of these corresponding steps 72-78 apply to the steps 112-118 of the method 110, with the exception that the method 110 is more applicable to use with structures experiencing change in a well. For example, the method 110 may be used to calculate heat transfer though a structure, cement integrity (presence of voids and cracks, bond quality), fluid migration through cement or the formation, reservoir evaluation, heat capacities, other thermal properties of multiple structures and/or fluids downhole, physical properties of tubulars or other structures or fluids downhole, etc.

Referring additionally now to FIG. 8, another sensing device 120 embodying principles of the invention is representatively and schematically illustrated. The sensing device 120 is at an enlarged scale and is depicted apart from its supporting structure and any associated sensors for illustrative clarity. However, it should be understood that the sensing device 120 may be positioned and supported in any manner, and may include sensors, such as the temperature sensors 60, 62, 64, in keeping with the principles of the invention.

Instead of heating the sensor surface 44 using light energy transmitted through the optical fiber 50 and converted to heat energy, in the sensing device 120 the light energy is transmitted directly through the diamond material 56 (or other light transmitting material, e.g., another transparent or at least translucent material) to the fluid 46 (or other substance) in contact with the surface 44. The fluid 46 responds to this energy input, and the response is detected as an indication of one or more properties of the fluid. Of course, the sensor surface 44 could be placed in contact with a substance other than a fluid, such as a tubular string material, cement, a formation, etc., in which case a property of that substance (and possibly a fluid therein) may be determined using the sensing device 120.

In one application, the light energy transmitted through the optical fiber 50, and thence through the diamond material 56, is reflected off of the fluid 46 (or other substance) back through the diamond material to the optical fiber. The reflected light is transmitted through the optical fiber 50 to a detector 122 at a remote location, such as the earth's surface or another location in the well. The reflected light may be analyzed to determine certain properties of the fluid 46.

In another application, the light energy transmitted through the diamond material 56 to the fluid 46 may cause at least a portion of the fluid to fluoresce. This fluorescence, or lack thereof, is detected by the detector 122 (such as a fluoroscope) in order to determine the composition, identity, source, water/oil ratio, or other property of the fluid 46.

In another application, the light energy transmitted through the diamond material 56 to the fluid 46 may excite the fluid to give off a spectrum indicative of the elemental composition of the fluid. This spectrum is detected by the detector 122 (such as a spectrometer) in order to determine the composition, identity, source, water/oil ratio, or other property of the fluid 46.

In another application, the light energy transmitted through the diamond material 56 to the fluid 46 may heat the fluid. Such heating of the fluid 46 and/or associated heating of the diamond material 56 may be detected directly or indirectly by sensors, such as the temperature sensors 60, 62, 64, to enable determination of properties of the fluid, such as density, velocity, thermal conductivity, or other property of the fluid.

Thus, the diamond material 56 may be considered as a "window" to permit the light energy transmitted through the optical fiber 50 to be also transmitted to the fluid 46 or other substance in contact with the sensor surface 44. Note that the diamond material 56 may be formed as a coating on a substrate as described above, although FIG. 8 shows the diamond material apart from any substrate.

Figure 9:
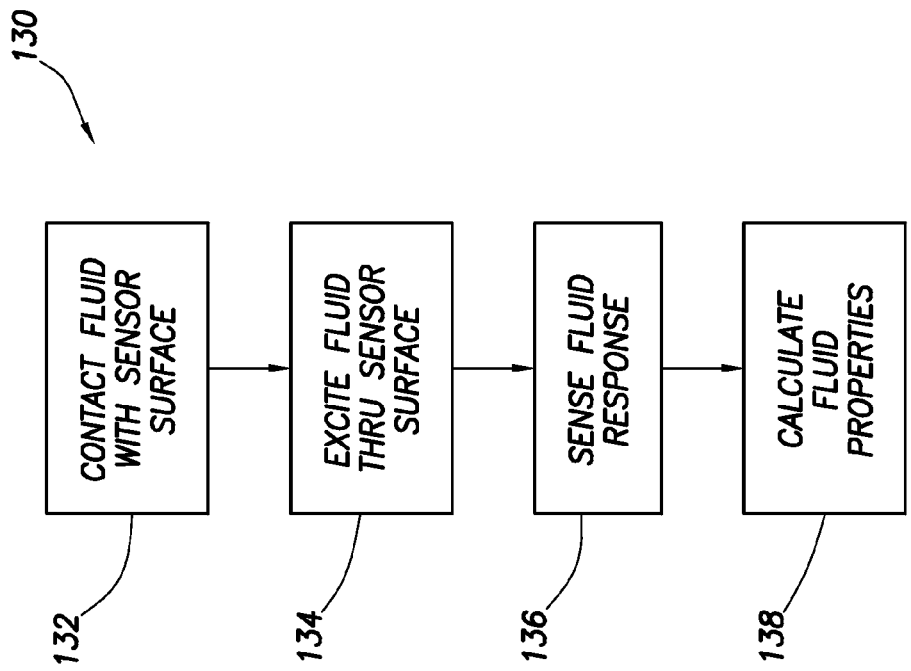
FIG. 9 is a flowchart of steps in a fourth method embodying principles of the present invention.

Referring additionally now to FIG. 9, a method 130 embodying principles of the invention is representatively illustrated in flowchart form. The method 130 may be performed using the sensing device 120 of FIG. 8, or other sensing devices may be used in keeping with the principles of the invention. The method 130 is described herein as if a fluid is in contact with the sensor surface 44, but it should be understood that any type of substance may be used instead of, or in addition to, a fluid.

In step 132, the fluid 46 contacts the sensor surface 44. In step 134, the fluid 46 is excited by transmission of light energy from the optical fiber 50 through the sensor surface 44 to the fluid. The fluid 46 may be heated by the light energy, a portion of the fluid may fluoresce, the fluid may give off a spectrum, etc. It should be understood that any response of the fluid 46 (or other substance) to the transmission of light energy through the sensor surface 44 is within the principles of the invention.

In step 136, the response of the fluid 46 to the light energy transmitted through the sensor surface 44 is sensed. This sensing step 136 may be performed in the well proximate the sensing device 120, or it may be performed at a remote location. For example, a fluoroscope or spectrometer 122 could be positioned at the earth's surface to detect the response of the fluid 46, or downhole sensors may be used, etc. In step 138, the response to the fluid 46 is used to calculate properties of the fluid, such as thermal or physical properties.

Note that the fiber optic sensing devices 40, 90, 120 as described herein do not obstruct any flow passage in the well, are convenient and reliable in operation, and do not require intervention into the well to operate. However, one or more of these benefits of the invention may be eliminated, if desired. For example, one of the sensing devices 40, 90, 120 could be used in a wireline conveyed production logging tool, which does obstruct a flow passage and requires an intervention into the well to operate. Thus, the applications of the principles of the invention are not limited to those described above.

Of course, a person skilled in the art would, upon a careful consideration of the above description of representative embodiments of the invention, readily appreciate that many modifications, additions, substitutions, deletions, and other changes may be made to the specific embodiments, and such changes are contemplated by the principles of the present invention. Accordingly, the foregoing detailed description is to be clearly understood as being given by way of illustration and example only, the spirit and scope of the present invention being limited solely by the appended claims and their equivalents.

What is claimed is:

1. A fiber optic sensing system for use in detecting at least one property of a substance or heat transfer characteristic of a location proximate to the substance in a subterranean well, the sensing system comprising:

an optical fiber connected to a sensing device in the subterranean well, wherein a surface of the sensing device is in contact with the substance, and wherein the surface is disposed on a substrate;
an energy converter which converts light energy transmitted by the optical fiber into heat energy in the substrate, whereby the surface of the sensing device is heated; and
a first temperature sensor which detects a temperature of the substance as heated by the surface.

2. The sensing system according to claim 1, wherein the substance is a fluid, and wherein the first temperature sensor detects the temperature of the fluid proximate the surface.

3. The sensing system according to claim 1, wherein the substance is a fluid, and wherein the first temperature sensor detects the temperature of the fluid downstream from the surface.

4. The sensing system according to claim 1, further comprising a second temperature sensor positioned remote from the first temperature sensor.

5. The sensing system according to claim 4, wherein the first temperature sensor detects the temperature of the substance proximate the surface, and the second temperature sensor detects a temperature of the substance remote from the surface.

6. The sensing system according to claim 5, wherein the second temperature sensor is downstream from the first temperature sensor.

7. The sensing system according to claim 5, wherein the second temperature sensor is upstream from the first temperature sensor.

8. The sensing system according to claim 1, wherein the surface comprises a diamond material.

9. The sensing system according to claim 1, wherein the energy converter is a black body interface.

10. The sensing system according to claim 1, wherein the substance is a tubular string material, and wherein the sensing system detects a thermal property of the tubular string material.

11. The sensing system according to claim 1, wherein the substance is a fluid in the well, and wherein the temperature of the substance as detected by the first temperature sensor is used to determine a thermal property of the fluid.

12. The sensing system according to claim 1, further comprising a laser transmitting the energy through the optical fiber.

13. The sensing system according to claim 12, wherein the laser is positioned at the earth's surface.

14. The sensing system according to claim 1, wherein the substance is a fluid within a tubular string in the well.

15. The sensing system according to claim 1, wherein the substance is a fluid external to a tubular string in the well.

16. The sensing system according to claim 15, wherein the fluid is disposed in an annulus between the tubular string and casing in the well.

17. The sensing system according to claim 15, wherein the tubular string is casing, and wherein the fluid is formation fluid.

18. The sensing system according to claim 1, wherein the substance is a hardenable material positioned in an annulus between a wellbore and casing in the well.

19. The sensing system according to claim 1, wherein the substance is a formation intersected by a wellbore of the well.

20. The sensing system according to claim 1, wherein the substance is a solid structure in the well.

21. The sensing system according to claim 20, wherein the structure is a tubular string.

22. The sensing system according to claim 1, wherein the sensing system includes multiple sensing devices distributed circumferentially about a tubular string in the well.

23. The sensing system according to claim 1, wherein the temperature of the substance as detected by the first temperature sensor is used to determine a physical level of an interface between different fluids flowing through a tubular string in the well.

24. The sensing system according to claim 1, wherein the sensing system includes multiple sensing devices distributed longitudinally along a tubular string in the well.

25. The sensing system according to claim 1, wherein the temperature of the substance as detected by the first temperature sensor is used to determine a physical level of an interface between different fluids in a formation intersected by the well.

26. The sensing system according to claim 1, wherein the substance is a hardenable material installed external to a tubular string in the well, and wherein the temperature of the substance as detected by the first temperature sensor is used to determine a quality of installation of the hardenable material.

27. The sensing system according to claim 26, wherein the temperature of the substance as detected by the first temperature sensor is used to determine a presence of a fluid in the hardenable material.

28. The sensing system according to claim 26, wherein the temperature of the substance as detected by the first temperature sensor is used to determine a presence of a void in the hardenable material.

29. The sensing system according to claim 26, wherein the temperature of the substance as detected by the first temperature sensor is used to determine a presence of a crack in the hardenable material.

30. The sensing system according to claim 1, wherein the temperature of the substance as detected by the first temperature sensor is used to determine a direction of flow of the substance through a tubular string in the well.

31. The sensing system according to claim 1, wherein the temperature of the substance as detected by the first temperature sensor is used to determine a rate of flow of the substance through a tubular string in the well.

32. The sensing system according to claim 1, wherein the temperature of the substance as detected by the first temperature sensor is used to determine a property indicative of an identity of the substance in the well.

33. The sensing system according to claim 1, wherein the temperature of the substance as detected by the first temperature sensor is used to determine a phase change in the substance in the well.

34. The sensing system according to claim 1, wherein the temperature of the substance as detected by the first temperature sensor is used to determine a ratio between different fluids included in the substance in the well.

35. The sensing system according to claim 1, wherein the substance is a tubular string material, and wherein the sensing system detects a thermal property of the tubular string material.

36. The sensing system according to claim 1, wherein the substance is a formation, and wherein the sensing system detects a thermal property of the formation.

37. The sensing system according to claim 36, wherein the sensing system detects a thermal property of a fluid in the formation.

38. The sensing system according to claim 36, wherein the sensing system detects a location of a fluid in the formation.

39. The sensing system according to claim 36, wherein the sensing system detects a presence of a fracture in the formation.

40. The sensing system according to claim 36, wherein the sensing system detects a location of a fracture in the formation.

41. The sensing system according to claim 1, wherein detection of the substance temperature by the sensing system is used to determine a heat transfer characteristic of a local well environment.

42. The sensing system according to claim 41, wherein the heat transfer characteristic is a heat capacity of the local well environment.

43. The sensing system according to claim 1, wherein the substance is a hardenable material positioned external to a tubular string, and wherein the temperature of the substance as detected by the first temperature sensor is used to determine a thermal property of the hardenable material.

44. A fiber optic sensing system for use in detecting at least one property of a substance or heat transfer characteristic of a location proximate to the substance in a subterranean well, the sensing system comprising:
  an optical fiber which transmits energy to a surface of a sensing device, the surface being heated as a result of the energy transmitted by the optical fiber; and
  a temperature sensor which detects a temperature of the substance as heated by the surface, wherein the energy transmitted by the optical fiber heats a substrate on which the surface is disposed, and wherein the surface comprises a diamond material attached to the substrate, the diamond material having greater thermal conductivity than the substrate.

45. The sensing system according to claim 12, wherein the laser is positioned in the well.

* * * * *